United States Patent [19]

Moore et al.

[11] 4,295,613
[45] Oct. 20, 1981

[54] APPARATUS FOR BREAKING BACTERIAL CELLS

[75] Inventors: W. Edward C. Moore, Blacksburg; James A. Blanks, Norfolk, both of Va.

[73] Assignee: VPI Educational Foundation, Blacksburg, Va.

[21] Appl. No.: 81,415

[22] Filed: Oct. 3, 1979

[51] Int. Cl.³ .............................................. B02C 17/14
[52] U.S. Cl. ........................................... 241/2; 241/23; 241/65; 241/179; 241/283; 435/287
[58] Field of Search .................. 252/360, 319, 347; 366/111; 435/287, 259, 803; 241/1, 2, 23, 65, 175, 181, 179, 170, 172, 283, 284; D24/32

[56] References Cited

U.S. PATENT DOCUMENTS

| | | | |
|---|---|---|---|
| D. 184,047 | 12/1958 | Francavillo | D24/32 X |
| 2,230,997 | 2/1941 | Chambers et al. | 241/2 X |
| 2,315,229 | 3/1943 | Schieferstein | 241/175 |
| 3,109,084 | 10/1963 | Walsh | D24/32 X |
| 3,172,546 | 3/1965 | Schreiner | 241/179 X |
| 3,291,400 | 12/1966 | Jensen | 241/176 X |
| 3,650,482 | 3/1972 | Andrews | 241/175 X |
| 4,118,801 | 10/1978 | Kraft et al. | 366/111 |

*Primary Examiner*—Mark Rosenbaum
*Attorney, Agent, or Firm*—Seidel, Gonda, Goldhammer & Panitch

[57] ABSTRACT

A multiple tube holder is suspended at the upper end on a frame so that the lower end can pivot through a small arc about a horizontal axis adjacent the upper end of the holder. A motor is connected to the lower end of the holder for pivoting the lower end of the holder through said small arc at a rate of approximately 1800 cycles per minute. A tray means is positioned below the holder for supporting a cooling liquid at a controlled temperature so that the lower end of the tubes on the holder will be immersed in the liquid to prevent destruction of proteins and enzymes released during cell breakage.

9 Claims, 3 Drawing Figures

U.S. Patent     Oct. 20, 1981     4,295,613
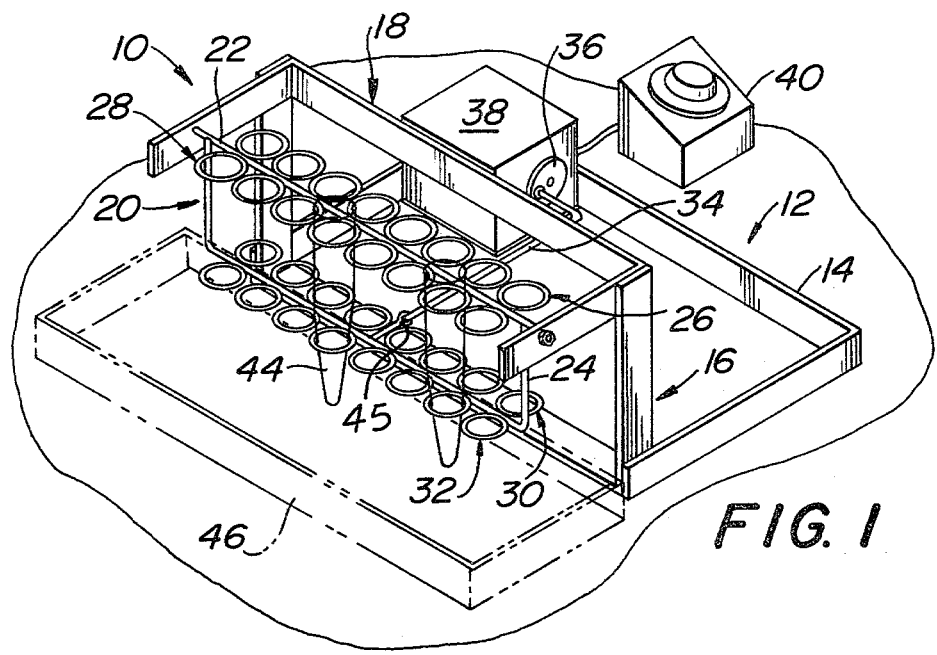
FIG. 1
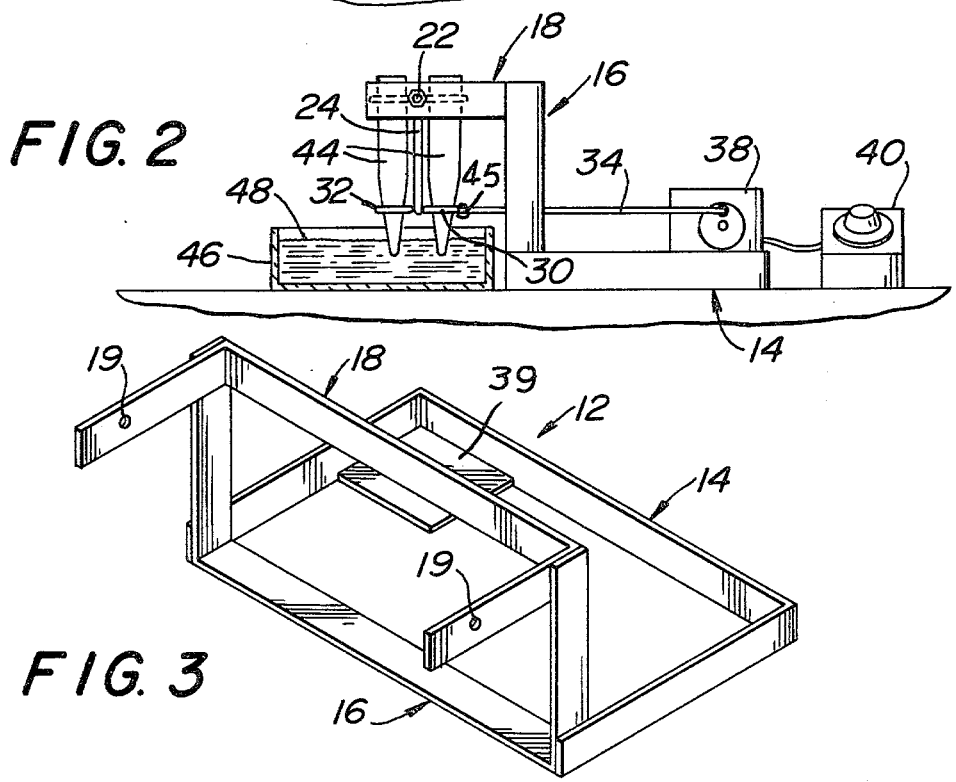
FIG. 2
FIG. 3

APPARATUS FOR BREAKING BACTERIAL CELLS

BACKGROUND

A large numer of different devices have been proposed heretofore for agitating fluids within a test tube. The devices proposed heretofore are ineffective to provide for the breakage of bacterial cells with fine glass beads. The device disclosed in U.S. Pat. No. 4,118,801 is representative of prior art designed only to mix fluid contents in a plurality of vessels. There is a need for simple and efficient devices for breaking bacterial cells with beads while allowing for the cells to be cooled in a simple and inexpensive manner so as to prevent the destruction of proteins and enzymes released during cell breakage. None of the prior art known to me is capable of performing in that manner.

SUMMARY OF THE INVENTION

The present invention is directed to apparatus for breaking bacterial cells while the cells are disposed within a vessel such as a test tube and in contact with fine beads or equivalent granular material. The apparatus includes a frame and a multiple tube holder suspended at its upper end on said frame so that the lower end of the holder can pivot through a small arc about a horizontal axis located adjacent the upper end of the holder. A motor means is connected to the lower end of the holder for pivoting the lower end of the holder through a small arc at a rate of approximately 1800 cycles per minute. A tray means is disposed below the holder for supporting a cooling liquid at a control temperature so that the lower end of the tubes on the holder will be immersed in the liquid to prevent destruction of proteins and enzymes released during cell breakage.

It is an object of the present invention to provide a novel apparatus for breaking bacterial cells which is simple, reliable and efficient for breaking bacterial cells without destruction of proteins and enzymes released during cell breakage.

Other objects will appear hereinafter.

For the purpose of illustrating the invention, there is shown in the drawings a form which is presently preferred; it being understood, however, that this invention is not limited to the precise arrangements and instrumentalities shown.

FIG. 1 is a perspective view of apparatus in accordance with the present invention.

FIG. 2 is a side elevation view of the apparatus shown in FIG. 1.

FIG. 3 is a perspective view of the frame.

Referring to the drawings in detail, wherein like numerals indicate like elements, there is shown apparatus in accordance with the present invention designated generally as 10. The apparatus 10 includes a base designated generally as 12.

As shown more clearly in FIG. 3, the base 12 is preferably made from three identical components welded or otherwise fixedly secured together. Thus, base 12 includes U-shaped frame members 14, 16 and 18 each made from any suitable metal having substantial weight such as iron, steel and the like. The U-shaped frame members 14 and 16 are in mutual perpendicular planes with the free ends of member 14 welded or otherwise fixedly secured to member 16 adjacent the bight thereof. The U-shaped frame member 18 is parallel to member 14 and has its bight portion fixedly secured to the free ends of member 16. The upper portion of the legs of U-shaped frame member 18 are provided with holes 19 to accept the tube support.

A multiple tube support designated generally as 20 is provided. The support 20 includes an upper rod 22 having its ends rotatably supported in the holes 19. The support 20 includes a U-shaped rod 24 having its free ends welded or otherwise fixedly secured to the rod 22. A first row of rings 26 which touch each other is secured to one side of rod 22. A second row of rings 28 which touch each other is secured to the other side of rod 22. The rows of rings 26, 28 and the rod 22 are all horizontally disposed. A third row of rings 30 is secured to one side of the bight portion of rod 24. A row of rings 32 are similarly attached to the opposite side of the bight portion of rod 24. Rings 30 and 32 are of the same size but smaller than rings 26, 28. The rings of row 26 are aligned with and larger than the rings of row 30. Likewise, the rings of row 28 are aligned with and larger than the rings of row 32. The sets of aligned rings cooperate to support a vessel such as a conical centrifuge tube or the like.

A connecting rod 34 has one end pivotably connected to the holder 20 by universal joint 45 adjacent the lower end thereof. The other end of rod 34 is connected to an eccentric 36 which in turn is connected to the output shaft of a motor 38. Motor 38 is controlled by a timer 40. Motor 38 may rest on platform 39 to provide stability to the frame. If further stability is needed a lead weight may be added or the frame may be bolted to a support.

The holder 20 is adapted to support a plurality of tubes 44 in an upright disposition. The tubes 44 are similar to conical centrifuge tubes in that they are tapered at their lower end which is the closed end of the tubes. The upper end of the tubes may be releasably closed in any convenient manner such as by a cork or the like. A tray 46 is supported below the holder 20 and is adapted to contain ice water 46 or some other liquid at a controlled temperature. Sufficient water 48 is provided so that the lower end of the tubes 44 is immersed therein.

The apparatus 10 was designed to violently shake the tips of the tubes 44 approximately 1800 times per minute with the small arc of travel of the tips of the tubes being about 5 millimeters while the tips are immersed in the ice water 48. Glass beads in the range of 70 to 110 micrometer diameter are introduced into the tubes along with the culture to be treated and any buffer solution needed to obtain solutions of bacterial constituents such as enzymes, proteins, carbohydrates, etc. The cells may be broken in the same tubes that they were harvested in with breaking of both gram positive and gram negative cells. There is no need for heating of the mixture nor is there any need for expensive cooling controls.

A distinct advantage of the present invention is its simplicity. The frame is made from three identical U-shaped metal members. The extent of the arc through which the tips moves is controlled by the amount of the eccentricity between rod 34 and the axis of the eccentric 36. Conventional motor 38 and timer 40 may be utilized. While the motor 38 is preferably operable at 1725 or 1800 rpm, it may be a variable speed motor. The apparatus is simple, reliable and effective while at the same time is inexpensive.

The present invention may be embodied in other specific forms without departing from the spirit or essential attributes thereof and, accordingly, reference should be made to the appended claims, rather than to the foregoing specification, as indicating the scope of the invention.

We claim:

1. A method of breaking bacterial cells within upright tubes having a tapered closed end comprising harvesting a culture containing bacterial cells in tubes, placing beads in the tubes containing bacterial cells to be broken, oscillating the tubes about a horizontal axis adjacent their upper ends at a rate of approximately 1725 to 1800 cycles per minute, and preventing destruction of proteins and enzymes released during cell breakage by immersing the closed ends of the tubes in a bath of cool liquid during said oscillating step.

2. A method in accordance with claim 1 including using beads having a diameter of 70–110 micrometers.

3. Apparatus for breaking bacterial cells within upright tubes comprising a frame having spaced pivots, a multiple tube holder for supporting upright tubes, means suspending the upper end of said holder on said frame pivots so that the lower end of the holder can oscillate through a small arc about a horizontal axis defined by said frame pivots, a motor connected to the lower end of said holder for oscillating the lower end of said holder through said small arc at a rate of approximately 1800 cycles per minute, said holder including first and second parallel rows of rings whose axes are vertically disposed, said holder including third and fourth rows of rings whose axes are vertically disposed, each ring of the third and fourth row being at an elevation below the elevation of the rings of the first and second rows, the hole of each ring of said third and fourth rows being aligned with the hole of one of the rings of the first and second rows, said first and second rows of rings being disposed at the approximate elevation of said horizontal axis, said third and fourth rows being at the approximate elevation where said motor is connected to said holder, said rings being adapted to support a plurality of upright tubes containing cells to be broken and beads of glass or sand which are introducable through the upper end of the tubes with the lower end of the tubes below the elevation of said third and fourth rows.

4. Apparatus for breaking bacterial cells within a vessel with beads or equivalent granular material, comprising a frame, a multiple vessel holder for supporting upright vessels, means suspending the upper end of said holder on said frame so that the lower end of said holder can pivot through a small arc about a horizontal axis adjacent the upper end of the holder, a motor means connected to the lower end of said holder for pivoting the lower end of the holder through said small arc at a rate of approximately 1725 to 1800 cycles per minute, and tray means below said holder for supporting a cooling liquid at a controlled temperature so that the lower end of the vessel supported by the holder will be immersed in the liquid to prevent destruction of proteins and enzymes released during cell breakage.

5. Apparatus in accordance with claim 4 wherein said frame is comprised of three U-shaped frame members interconnected to form a generally Z-shaped frame.

6. Apparatus in accordance with claim 4 wherein the holder includes an upper rod member pivotally supported at its ends by said frame, first and second rows of rings attached to said rod member, a U-shaped rod member having its free ends connected to said first-mentioned rod member, third and fourth rows of rings attached to the bight portion of said U-shaped rod member, each ring of each row being aligned with a ring in another row so as to define concentric rings for confining and supporting a vessel in the form of a tube closed at its lower end and releasably open at its upper end.

7. Apparatus in accordance with claim 4 wherein said holder supports a plurality of vessels each having beads of sand or glass therein with the diameter of the beads being 70 to 110 micrometers in diameter.

8. Apparatus for breaking bacterial cells within upright tubes comprising a frame having spaced pivots, a multiple tube holder, means suspending the upper end of said holder on said frame pivots so that the lower end of the holder can oscillate through a small arc about a horizontal axis defined by said pivots, a motor connected to the lower end of said holder for oscillating the lower end of said holder through said small arc at a rate of approximately 1800 cycles per minute, said holder being adapted to support a plurality of tubes containing cells to be broken and beads of glass or sand which are introducable through the upper end of the tubes, and tray means below said holder for supporting a cooling liquid at a controlled cool temperature so that the lower end of the tubes on the holder will be immersed in the liquid to prevent destruction of proteins and enzymes released during cell breakage.

9. Apparatus in accordance with claim 8 wherein said holder includes first and second parallel rows of rings whose axes are vertically disposed, said holder including third and fourth rows of rings whose axes are vertically disposed, each ring of the third and fourth row being at an elevation below the elevation of the rings of the first and second rows, each ring of said third and fourth rows being aligned with one of the rings of the first and second rows, said first and second rows of rings being disposed at the approximate elevation of said horizontal axis, said third and fourth rows being at the approximate elevation wherein said motor is connected to said holder.

* * * * *